United States Patent [19]

Harrison et al.

[11] Patent Number: 5,236,960
[45] Date of Patent: Aug. 17, 1993

[54] WATER-BLOWN POLYURETHANE INTEGRAL SKIN FOAM

[75] Inventors: Richard P. Harrison, Lincoln Park; Michael Scarpati, Trenton; Thirumurti Narayan, Grosse Ile; Blair J. Zagata, Troy, all of Mich.

[73] Assignee: BASF Corporation, Parsippany, N.J.

[21] Appl. No.: 5,683

[22] Filed: Jan. 19, 1993

Related U.S. Application Data

[62] Division of Ser. No. 07/902,137, Jun. 22, 1992.

[51] Int. Cl.$^5$ .................................. C08J 0/00
[52] U.S. Cl. ................................. 521/51; 252/182.22; 521/159; 521/160; 521/901; 528/67; 528/76; 528/77; 560/25; 560/26; 560/334
[58] Field of Search ............... 521/51, 159, 160, 901; 528/67, 76, 77; 252/182.22

[56] References Cited

FOREIGN PATENT DOCUMENTS 51-8395 1/1976 Japan .

OTHER PUBLICATIONS

Journal of Polymer Science: Polymer Chemistry Edition, vol. 14, 1976, pp. 2043-2059, W. J. Jackson, Jr., et al., "Liquid Crystal Polymers. I. Preparation and Properties of p-Hydroxybenzoic Acid Copolyesters".

*Primary Examiner*—Morton Foelak
*Attorney, Agent, or Firm*—Dennis V. Carmen

[57] ABSTRACT

The invention relates to water blown integral skin polyurethane foams made with a particular isocyanate quasi-prepolymer and resin side ingredients to yield a foam having good overall mechanical properties. The isocyanate quasi-prepolymer component of the present invention comprises from 0.5 weight percent to 30.0 weight percent or less uretonimine-carbodiimide-modified diphenylmethane diisocyanate, from 50 weight percent to 80 weight percent 4,4'-diphenylmethane diisocyanate and reacted with from 15 weight percent to 40 weight percent of a polyether polyol containing predominately secondary hydroxyl groups and having an average molecular weight from about 2,000 to 10,000, an average functionality from 1.5 to about 3.2, and a hydroxyl number from about 20 to 60, and optionally with a low molecular weight diol in an amount of from 1.0 weight percent to 10 weight percent, the weight percentages based on the weight of the quasi-prepolymer reactants. The resin side component comprises a high molecular weight polyether compound having isocyanate reactive hydrogens and average molecular weights from about 2,000 to about 10,000 and an average functionality from 1.5 to about 3.2, water as a blowing agent in an amount of from 0.25 weight percent to 3 weight percent, an effective amount of polyurethane and/or polyurea promoting catalyst, a surfactant, and a chain extender, and optionally a mono- or di- functional alcohol composition having from 8 to about 30 carbon atoms.

The components, when injected or poured into a preheated mold, can tolerate mold temperatures from 105° F. to 135° F. and can be demolded in less than 150 seconds to yield an integral skin foam having little or no bubbles or pores visible to the eye. The foam produced thereby has a compression set of 30 percent or less, high tensile strength, and high tear strength.

15 Claims, No Drawings

WATER-BLOWN POLYURETHANE INTEGRAL SKIN FOAM

This is a division of application Ser. No. 07/902,137 filed Jun. 22, 1992.

The present invention relates to water-blown polyurethane integral skin foams and elastomers, more particularly to water-blown polyurethane integral skin foams having low compression set, good mechanical properties, and good processing characteristics, especially for use as steering wheels.

BACKGROUND OF THE INVENTION.

It is generally known that polyurethane foams can be manufactured using water as a blowing agent. The reaction of an isocyanate group with water yields an urea group and evolves carbon dioxide gas, acting as the agent responsible for the foaming action. The presence of urea groups, however, hardens the foam and leads to poor compression set values. In response to this problem, polyphenylene polymethylene polyisocyanate (polymeric-MDI) has been added to improve compression set; but the improvement has come at the expense of other physical properties, such as elongation, tear strength, and tensile strength. Therefore, the inventors herein have sought to make a water-blown polyurethane integral skin foam which simultaneously possesses good compression set, elongation, tear strength, and tensile strength comparable to a CFC-blown integral skin polyurethane foam, and to formulate a system that processes well, is not sensitive to minor processing conditions, and demolds quickly.

SUMMARY OF THE INVENTION

It is an object of the invention to make a polyurethane integral skin foam blown with water as a replacement for chlorofluorocarbon-blown polyurethane integral skin foams. The water-blown foam must simultaneously possess good mechanical properties, compression set, and other mechanical properties, especially tear strength, tensile strength, and elongation.

It is a further object of the invention to make a water-blown integral skin polyurethane foam having good processing characteristics, namely, low demold times, higher limitation mold temperatures, and wide processing windows to allow for larger margins of error in formulation and processing conditions.

It has now been discovered that a particular isocyanate quasiprepolymer when reacted with particular resin side ingredients yields a water-blown integral skin foam having good overall mechanical properties. The isocyanate quasi-prepolymer component of the present invention comprises from 0.5 weight percent to 30.0 weight percent, preferably from 0.5 to less than 12.5 weight percent uretonimine-carbodiimide-modified diphenylmethane diisocyanate, from 50 weight percent to 80 weight percent 4,4'-diphenylmethane diisocyanate; reacted with from 15 weight percent to 40 weight percent of a polyether polyol containing predominately secondary hydroxyl groups and having an average molecular weight from about 2,000 to 10,000, an average functionality from 1.5 to about 3.2, and a hydroxyl number from about 20 to 60, and optionally with a low molecular weight diol in an amount of from 1.0 weight percent to 10 weight percent, the weight percentages based on the weight of the quasi-prepolymer reactants. The quasi-prepolymer may optionally be mixed with 1 weight percent to 30 weight percent polyphenylene polymethylene polyisocyanate as a blend of quasi-prepolymer/polymeric MDI. The resin side component comprises a high molecular weight polyether compound having isocyanate reactive hydrogens and average molecular weights from about 2,000 to about 10,000 and an average functionality from 1.5 to about 3.2, water as a blowing agent, an effective amount of polyurethane and/or polyurea promoting catalyst, a surfactant, and a chain extender, and optionally a mono- or difunctional alcohol composition having from 8 to about 30 carbon atoms. The components, when injected or poured into a preheated mold, can tolerate mold temperatures from 105° F. to 135° F., preferably 115° F. to 135° F. and can be demolded in less than 150 seconds to yield an integral skin foam having little or no bubbles or pores visible to the eye. The process is not particular to a narrow range of mold temperatures, does not require a large number of vent holes, and is tolerant of a wide range in component temperatures spanning from 75° F. to 95° F.

DETAILED DESCRIPTION OF THE INVENTION

The integral skin foams produced in this invention are flexible and have overall molded densities ranging from 20 pcf to 40 pcf. Applications of the foam include automotive parts such as steering wheels, armrests, horn covers, headrests, or trim and nonautomotive applications such as shoe soles, gaskets, or furniture parts.

The Quasi-prepolymer Component

The isocyanate quasi-prepolymer of the invention is prepared by reactinq a mixture or blend of 4,4'-diphenylmethane diisocyanate (4,4'-MDI) and uretonimine-carbodiimide-modified 4,4'-diphenylmethane diisocyanate with a composition bearing isocyanate reactive hydrogens.

The carbodiimide modification of 4,4'-MDI can be represented by the formulas:

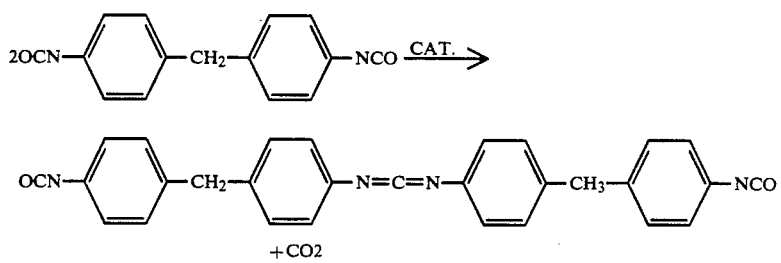

This carbodiimide then reacts predominately with further unconverted 4,4'-MDI to form uretonimine-modified 4,4'-MDI represented by the following formula:

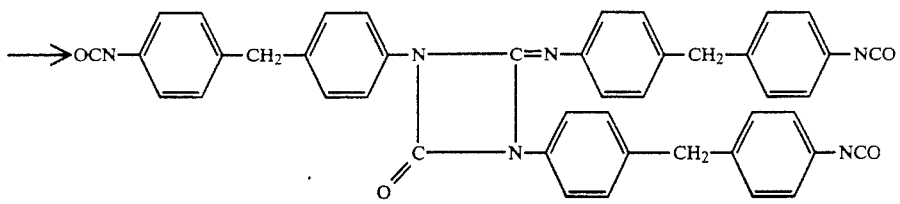

The uretonimine-carbodiimide-modified polyisocyanate is obtained by employing well-known carbodiimide-promoting catalysts in the polyisocyanate to convert the isocyanate to the carbodiimide at temperatures from 50° C. to 250° C., which then proceeds to react with further unconverted polyisocyanates at room temperature to form a uretonimine-modified polyisocyanate. The polyisocyanate employed in the conversion to carbodiimide and uretonimine is 4,4'-MDI. The extent to which the carbodiimide modification is further converted to the uretonimine form varies with the reaction temperature and the time in which the reaction mixture is allowed to stand at room temperature. However, as employed in the invention, a "uretonimine-carbodiimide-modified 4,4'-MDI" is one which contains a uretonimine/carbodiimide ratio greater than 50:50, preferably a ratio ranging from 85-99:15-1 by weight. Although a 100 weight percent uretonimine-modified 4,4'-MDI may be employed, the conversion from carbodiimide to uretonimine does not usually go to completion; and there normally remains some carbodiimide present in the MDI. Typical catalysts useful in the conversion of a diisocyanate to carbodiimide-modified diisocyanate include phospholene 1-oxides and 1-sulfides, diaza- and axaza-phospholanes and phosphorinanes, triaryl arsines, and trialkyl phosphates as described in U.S. Pat. No. 4,743,626, herein incorporated by reference.

During the process of making the uretonimine-carbodiimide-modified MDI, it is preferred that about 5 weight percent to 35 weight percent, more preferably from 20 weight percent to 30 weight percent of the MDI is converted to the uretonimine-carbodiimide form. The MDI composition containing the uretonimine-carbodiimide-modified MDI is preferably blended with further MDI prior to reaction with the polyether polyol to yield the desired quasi-prepolymer, or the conversion to uretonimine-carbodiimide MDI may take place in the total amount of MDI desired prior to reacting with polyol, thereby eliminating the need to blend with further MDI. The amount of uretonimine-carbodiimide-modified MDI present in the quasi-prepolymer is from 0.5 weight percent to 30 weight percent, preferably from 0.5 to less than 12.5 weight percent, more preferably from 1.0 weight percent to 7.0 weight percent, based on the weight of all ingredients in the quasi-prepolymer An alternative embodiment uses from 3 weight percent to 12.5 weight percent of uretonimine-carbodiimide-modified MDI.

The MDI utilized in the invention comprises 4,4'-MDI, 2,4'-MDI, 2,2'-MDI, or mixtures of these isomers. The amount of 4,4'-MDI isomer in the quasi-prepolymer is from 50 weight percent to 80 weight percent, preferably from 65 weight percent to 75 weight percent, most preferably about 70 weight percent, based on the weight of all ingredients in the quasi-prepolymer. The amount of 2,4'-MDI and 2,2'-MDI isomers is advantageously less than 4 weight percent, more preferably less than 1 weight percent of the quasi-prepolymer. Thus, the MDI in the quasi-prepolymer is essentially 4,4'-MDI.

The remaining portion of the quasi-prepolymer comprises a high molecular weight polyether polyol composition in an amount of from 15 weight percent to 40 weight percent of the quasi-prepolymer, preferably in an amount of from 20 weight percent to 30 weight percent. The polyether polyol has a high average molecular weight ranging from 2,000 to 10,000, preferably from 2,500 to 5,000, has an average functionality from 1.50 to 3.2, and a hydroxyl number from 20 to 60. Since a water-blown polyurethane foam produces hard urea segments, it has been found that it is necessary to employ high molecular weight polyether polyols to soften up the polyurethane polymer.

The polyether polyol composition of the invention contains a predominant amount of secondary hydroxyl groups, with a composition consisting of all secondary hydroxyl groups being preferred. By a predominant amount of secondary hydroxyl group containing polyether polyol composition, it is meant that no more than about 3.5 weight percent of the polyether polyol should be terminated with polyoxyethylene groups or groups producing primary hydroxyl termination. It is acceptable to add ethylene oxide to prepare a heteric or internal block polyether polyol so long as no more than 3.5 weight percent of the polyol is terminated with primary hydroxyl groups. Although it is within the scope of the invention to add the above minor amounts of ethylene oxide to an initiator molecule as a cap, it is preferable to prepare a polyoxyalkylene polyether polyol exclusively containing secondary hydroxyl groups. It is believed that the tear strength, compression set, and tensile strength of the molded article tend to degrade when more than minor amounts of ethylene oxide as a cap are added in the preparation of the polyether polyol used in the formation of the quasi-prepolymer. Thus, a polyether polyol prepared by oxypropylating an initiator molecule without addition of any ethylene oxide yields a prepolymer, which when used in the resin described below, produces an integral skin foam having optimal mechanical properties.

Methods of making polyether polyols ar well known and include those polyethers prepared from the base catalyzed addition of an alkylene oxide such as propylene oxide or butylene oxide, preferably propylene oxide, to an initiator molecule containing, on the average, two or more active hydrogens. The polyoxyalkylene polyether polyols may be prepared by any known process such as, for example, the process disclosed by Wurtz in 1859 and *Encyclopedia of Chemical Technology*, Vol. 7, pp 257-262, published by Interscience Publishers, Inc. (1951) or in U.S. Pat. No. 1,922,459, hereby incorporated by reference. Examples of initiator molecules are diethylene glycol, ethylene glycol, dipropylene glycol, propylene glycol, trimethylene glycol, 1,2- butanediol, 1,3-butanediol, 1,4-butanediol, 1,4-pentanediol, 1,5-pentanediol, 1,6-hexanediol, 1,7-heptanediol, glycerine, 1,1,1-trimethylolpropane, 1,1,1-trimethylolethane, 1,2,6-hexanetriol, or triethylolpropane. Particularly preferred initiators include trimethylolpropane, propylene glycol, and blends of polyoxyalkylene polyether polyols initiated thereby, with propylene glycol being most preferred.

Suitable alkylene oxides propylene oxide, butylene oxide, amylene oxide, and mixtures of these oxides. Preferred is the reaction product of all propylene oxide with one of the aforementioned initiators, preferably propylene glycol, to yield a polyether polyol having only secondary hydroxyl groups. In one embodiment, the polyether polyol has a molecular weight from 3,000 to 3,600, an average functionality from about 1.7 to 2.0, a hydroxyl number from 26 to 37, and prepared by adding propylene oxide to a propylene glycol initiator.

Also suitable as the polyol are polymer-modified polyols, in particular, the so-called graft polyols in which the carrier polyol contains substantially all secondary hydroxyl groups. Graft polyols are well known to the art and are prepared by the in situ polymerization of one or more vinyl monomers, preferably acrylonitrile and styrene, in the presence of a polyether or polyester polyol, particularly polyols containing a minor amount of natural or induced unsaturation. Methods of preparing such graft polyols may be found in columns 1–5 and in the Examples of U.S. Pat. No. 3,652,639; in columns 1–6 and the Examples of U.S. Pat. No. 3,823,201; particularly in columns 2–8 and the Examples of U.S. Pat. No. 4,690,956; and in U.S. Pat. No. 4,524,157, all of which patents are herein incorporated by reference.

The quasi-prepolymer is prepared over a one- to five-hour period at 50° C. to 80° C., preferably at 60° C. to 70° C., by introducing the desired quantity of polyether polyol at a constant rate over about a one-hour period into a preheated reactor containing the desired quantity of MDI and uretonimine-carbodiimide-modified MDI. The reaction is carried out in the presence of a catalyst deactivator, at reaction temperatures or lower, and preferably in an inert gas atmosphere. The reaction is checked after a period of time to determine the free NCO content, and heating is continued until the desired NCO content is attained. It is preferable that the quasi-prepolymer has an NCO content of 10 to 32 weight percent, more preferably from 20 to 30 weight percent, most preferably from 22 to 26 weight percent.

Suitable catalyst deactivators include salts such as magnesium chloride dihydraite, acid chlorides such as benzoyl chloride and acetyl chloride, acids such as hydrochloric acid, oxalic acid, phosphoric acid, benzenesulfonic acid, toluenesulfonic acid, methanesulfonic acid or trifluoromethanesulfonic acid, sulfonyl chlorides such as benzenesulfonyl chloride, toluenesulfonyl chloride, and the like. Other deactivators which may be employed are such agents as dimethylsulfate, alkyl o,p-toluenesulfonates, methylchloride and similar compounds as disclosed in U.S. Pat. Nos. 3,769,318 and 4,738,991, each herein incorporated by reference.

Another feature of the invention is the preparation of a quasi-prepolymer having increased viscosity and greater storage stability where the quasi-prepolymer is stable at 10° C. for two weeks. This is accomplished by blending a low molecular weight diol, triol, or tetrol of less than 175 in an amount of from 1.0 weight percent to 10 weight percent, based on the weight of the quasi-prepolymer, with the polyether polyol, and subsequently introducing the polyether polyol/diol blend into the reactor containing the MDI according to the aforementioned method of reaction In addition, the storage stability is enhanced by increasing the levels of uretonimine-carbodiimide modified 4,4'-MDI in the quasi-prepolymer. Suitable diols include dihydric initiators employed in the preparation of the polyether polyol, with preferable diol being dipropylene glycol and ethylene glycol. It is also preferable to add the low molecular weight diol to the MDI in an amount of from 4 weight percent to 6 weight percent. During the course of the reaction, the free NCO content and viscosity may be checked to determine whether the desired target has been achieved, namely, an NCO content as described above and an increased viscosity greater than about 200 cP, preferably greater than 275 cP.

An optional feature of the invention comprises blending polymeric-MDI with the quasi-prepolymer to make a 1-30/70-99 polymeric-MDI/quasi-prepolymer blend. The polymeric MDI contains approximately 35 weight percent to 65 weight percent 4,4'-diphenylmethane diisocyanate, 10 weight percent to 20 weight percent three-ringed aromatic polyisocyanates, and 25 weight percent to 45 weight percent higher functional oligomers. However, excellent mechanical properties such as compression set have been achieved in the absence of any polymeric MDI reacted with o blended with the quasi-prepolymer.

The Resin Component

The resin side component comprises a blend of a composition having isocyanate reactive hydrogens and of high molecular weight, water, one or more polyurethane catalysts, a surfactant, a chain extender, and optionally a mono-functional alcohol composition The composition having isocyanate reactive hydrogens has an average molecular weight of from 2,000 to 10,000, preferably 3,500 to 6,000, most preferably from about 4,000 to about 5,000, and an average functionality from 1.5 to 3.2. Suitable compositions comprise polyhydroxyl-containing polyesters, polyoxyalkylene polyether polyols, polyhydroxy-terminated polyurethane polymers, polyhydroxyl-containing phosphorus compounds, and alkylene oxide adducts of polyhydric sulfur-containing esters, polyacetals, aliphatic polyols or diols, ammonia, and amines including aromatic, aliphatic and heterocyclic amines as well as mixtures thereof. Alkylene oxide adducts of compounds which contain two or more different groups within the above-identified classes may be used such as amino alcohols which contain an amino group and a hydroxyl group. Also, alkylene oxide adducts of compounds which contain 1-SH group and one —OH group as well as those which contain an amino group and a —SH group may be used.

Any suitable hydroxy-terminated polyester may be used such as are obtained, for example, from polycarboxylic acids and polyhydric alcohols. Any suitable polycarboxylic acid may be used such as oxalic acid, malonic acid, succinic acid, glutaric acid, adipic acid, palmelic acid, suberic acid, azelaic acid, subacic acid, brassylic acid, thapsic acid, maleic acid, fumaric acid, glutaconic acid, alpha-hydromuconic acid, betahydromuconic acid, alpha-butyl-alpha-ethyl-glutaric acid, alpha, beta-diethylsuccinic acid, isophthalic acid, terephthaic acid, hemimellitic acid, and 1,4-cyclohexane dicarboxylic acid and mixtures thereof. Any suitable polyhydric alcohol may be used such as ethylene glycol, propylene glycol, trimethylglycol, 1,2-butanediol, 1,3-butanediol, 1,4-butanediol, 1,2-pentanediol, 1,4-pentanediol, 1,5-pentanediol, 1,6-hexanediol, 1,7-heptanediol, glycerol, 1,1,1-trimethylolpropane, 1,1,1-trimethylolethane, 1,2,6-hexanetriol, alphamethyl glucoside, pentaerythritol and sorbitol and mixtures thereof. Also included within the term "polyhydric alcohol: are compounds derived from phenol such as 2,2-bis(4-hydroxyphenyl)propane, commonly known as Bisphenol A.

Any suitable polyoxyalkylene polyether polyol may be used as the polymerization product of an alkylene oxide with a polyhydric alcohol. Any suitable polyhydric alcohol may be used such as those disclosed above for use in the preparation of the hydroxy-terminated polyesters and for the preparation of the quasi-prepolymer. Any suitable alkylene oxide may be used such as ethylene oxide, propylene oxide, butylene oxide, amylene oxide, and mixtures of these oxides. The polyalkylene polyether polyols may be prepared from other starting materials such as tetrahydrofuran and alkylene oxide-tetrahydrofuran mixtures; epihalohydrins such as epichlorohydrin; as well as arylalkylene oxides such as styrene oxide. The polyalkylene polyether polyols may also have either primary or secondary hydroxyl groups.

Polyethers are preferred and preferably include the alkylene oxide addition products of dipropylene glycol, trimethylolpropane, glycerine, propylene glycol, dipropylene glycol, and 2,2-bis(4-hydroxyphenyl)propane and blends thereof having equivalent weight of from 100 to 5,000.

Suitable polyhydric polythiol ethers which may be condensed with alkylene oxides include the condensation product of thiodiglycol or the reaction product of a dicarboxylic acid such as is disclosed above for the preparation of the hydroxyl-containing polyesters with any other suitable thioether glycol.

The hydroxyl-containing polyester may also be a polyester amide such as is obtained by including some amine or amino alcohol in the reactants for the preparation of the polyesters. Thus, polyester amides may be obtained by condensing an amine alcohol such as ethanol amine with the polycarboxylic acids set forth above or they may be made using the same components that make up the hydroxyl-containing polyesters with only a proportion of the components being a diamine such as ethylenediamine.

Polyhydroxyl-containing phosphorous compounds which may be used include those compounds disclosed in U.S. Pat. No. 3,639,542. Preferred polyhydroxyl-containing phosphorous compounds are prepared from alkylene oxides and acids of phosphorous compounds having a $P_2O_5$ equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above. Suitable aliphatic thiols which may be condensed with alkylene oxides include alkane thiols containing at least 2-SH groups as 1,2-ethanedithiol, 1,2-propanedithiol, 1,3-propanedithiol, and 1,6-hexanedithiol; alkane thiols such as 2-butene-1,4-dithiol; and alkane thiol such as 3-hexane-1,6-dithiol.

Suitable amines which may be condensed with alkylene oxides include aromatic amines such as aniline, o-chloroaniline, p-amino aniline, 1,5-diaminonaphthalene, methylene dianiline, the condensation products of aniline and formaldehyde, and diamino toluene; aliphatic amine such as methylamine, tris-isopropanol amine, ethylene diamine, 1,3-diaminopropane, 1,3-diaminobutane, and 1,4-diaminobutane.

The polyurethane foams of the present invention may also be prepared by the reaction of a graft copolymer polyol with the quasi-prepolymer. Suitable graft copolymers are such as those described above in the preparation of the quasi-prepolymer.

Chain extending agents employed in the preparation of the polyurethane foams include those compounds having at least two functional groups bearing active hydrogen atoms such as water, hydrozene, primary and secondary diamines, amino alcohols, amino acids, hydroxy acids, glycols or mixtures thereof. A preferred group of chain extending agents includes ethylene glycol, 1,4-butanediol, diethylene glycol, or propylene glycol. Other chain extenders include primary and secondary diamines which react more readily with the polyisocyanates of the instant invention than does water. These include phenylenediamine, ethylenediamine, diethylenetriamine, N-(2-hydroxypropyl)ethylenediamine, N,N'-di(2-hydroxypropyl)ethylenediamine, piperazine, 2-methylpiperazine. The chain extender is preferably present in amounts from 2.0 weight percent to 10 weight percent, more preferably from 4.0 weight percent to 7.0 weight percent.

Any suitable catalyst may be used including tertiary amines such as, for example, triethylenediamine, N-methylmorpholine, N-ethylmorpholine, diethylaminoethanol, N-lauryl morpholine, 1-methyl-4(dimethylaminoethyl)piperazine, 3-methoxy-N,N'-dimethylpropylamine, N,N,N'-trimethylisopropyl propylene diamine, N,N,N,N'-tetraethylpropylenediamine, dimethylbenzylamine, mixtures thereof and the like. Examples of such commercially available catalysts are the DABCO ® catalyst series available through Air Products Corp. Other suitable catalysts are, for example, tin compounds such as stannous chloride, tin salts of carboxylic acids, such as dibutyl tin di-2-ethylhexanoate and stannous octoate, available under the FOMREZ ® trademark, and other organic metallic compounds such as are disclosed in U.S. Pat. No. 2,846,408. The amount of catalyst is preferably from 0.01 weight percent to 2.0 weight percent based on the weight of the resin component.

A surface active agent is generally necessary for production of integral skin polyurethane foam having a well-defined pore-free skin and a suitable well-formed open-celled core. Numerous surface active agents have been found satisfactory, such as those which aid in homogenizing the starting materials, regulate cell structure, and/or act as wetting agents. Nonionic surfactants are preferred. Of these, the nonionic surface active agents prepared by the sequential addition of propylene oxide and then ethylene oxide to the propylene glycol and the solid or liquid organo silicones have been found particularly desirable. Examples include siloxane oxyalkylene heterol polymers and other organic polysiloxanes, oxyethylated alkyl phenol, oxyethylated fatty alcohols, paraffin oils, castor oil ester, phthalic acid esters, ricindolic acid ester, and Turkey red oil, as well as cell regulators such as paraffins. Other surface active agents which are operative and include polyethylene glycol ethers of long chain alcohols, tetra amine or alkanol amine salts of long chain alkyl acid sulfate esters, alkyl sulfonic esters, and alkyl arylsulfonic acids.

A long chained branched and/or unbranched aliphatic composition having from about 6 to about 20 carbons, preferably 10 to 15 carbons, may be used according to the present invention as a surfactant/wetting agent either in addition to the above mentioned surfactants or as the surfactant of the foam system. Alcohols of this type are known to those skilled in the art. The types of alcohols contemplated are commonly produced by hydroformylation of an olefin in the presence of a catalyst such as a cobalt known as the oxo process. The preferred carbon range for use as a surfactant is from $C_{12}$–$C_{15}$, although other low carbon alcohols in the plasticizer range are also useful. Examples of suitable oxo-alcohols include lin $C_{12}$–$C_{13}$, lin $C_{13}$–$C_{15}$, lin $C_{12}$–$C_{13}$–$C_{14}$–$C_{15}$, and lin $C_{14}$–$C_{15}$. The oxo-alcohols are typically supplied as isomeric mixtures, these being suitable for use in the invention. Longer chained alcohols are made by ethoxylating shorter chained alcohols and may optionally comprise ethylene oxide-propylene oxide adducts of the shorter chained alcohols Examples of some commercially available products include LIAL 125 from Enichem Augusta Spa or NEODOL® 25 produced by Shell. The alcohol composition is preferably present in amounts of from 0.3 to 1.0 weight percent.

The main blowing and density controlling agent used according to the present invention is water. For the purpose of the invention, water is present in amounts effective to make a part having the desired density, for example, up to and including 2.0 pbw based on the total weight of the resin component for most applications. It is preferably present in amounts from about 0.4 weight percent to 1.0 weight percent based on the total of the resin component. The phrase "water-blown" is meant to exclude any other blowing agent besides water. Although water is preferably the sole blowing agent used in the present invention, other blowing agents may be admixed with water, including reactive blowing agents such as formic acid or tertiary alcohols, or physically active blowing agents such as the volatile hydrocarbons and fluorocarbons, especially those fluorocarbons having an ozone depletion potential of 0.05 or less, in which case the foam is referred to for purposes of this invention as a "polyurethane integral skin foam blown with water."

Additives may optionally be used in the process of the present invention and include known pigments such as carbon black, dyes, and flame retarding agents (e.g., trischloroethyl phosphates or ammonium phosphate and polyphosphate), stabilizers against aging and weathering, plasticizers, such as gamma butyrolactone, fungistatic and bacteriostatic substances, and fillers.

The water-blown polyurethane system is run at an index of 60 to 150, preferably 90 to 115, more preferably 95 to 105, most preferably at 100. The index of the system is defined as the NCO/active hydrogen ratio equivalent multiplied by 100. In calculating the quantity of active hydrogens present, all active hydrogen-containing compounds other than non-dissolving solids are taken into account, including polyols, chain extenders, functional plasticizers, etc.

The mechanical parameters of the instant process are flexible and depend on the final application of the integral skin polyurethane foam. The reaction system is versatile enough that it may be made in a variety of densities and hardnesses. The system may be introduced into a mold in a variety of ways known to those skilled in the art. It may be shot into a preheated closed mold via high pressure injection technique. In this manner, it processes well enough to fill complex molds at low mold densities (from 20 pcf to 40 pcf, preferably from 25 pcf to 32 pcf). It may also be run using a conventional open mold technique wherein the reaction mixture or system is poured or injected at low pressure or atmospheric pressure into a preheated open mold. In the instant process, the system may be run at mold temperatures from about 85° F. to about 135° F. with from about 115° F. to about 135° F. being preferred. Depending on the shape and complexity of the part to be molded, the mold may be rotated from 0° to 90° off of the horizontal axis using gravity to reduce skin defects, promote even flow, and promote a more uniform cell structure.

The water-blown integral skin foams of the present invention may be used as steering wheels and preferably possess the following mechanical properties at overall molded densities from 25–45 pcf, preferably 25–35 pcf, more preferably from 28–31 pcf, and optionally at skin thicknesses advantageously 0.1 inch or less, more preferably less than 0.08 inch; skin and core tensile strengths of 400 psi or more, more preferably 500 psi or more; skin and core split tear strengths of 18 pi or more, more preferably 20 pi or more; skin and core Graves tear strength of 50 pi or more, more preferably 70 pi or more; skin and core elongation of 140 percent or more, more preferably 190 percent or more, and a compression set of 30 percent or less, more preferably 25 percent or less, most preferably 18 percent or less. The thickness of the skin may be controlled in part by reducing the number and/or size of the vent holes in the mold as discussed below. It was surprising to find that even at skin thicknesses of 0.1 inch or less, the skin formed using the raw materials of the invention is free of surface defects such as pore information, bubbles, and skin delamination; and the skin has high strength and exhibits a taber abrasion loss of less than 200 mg.

Another feature of the invention allows one to utilize a mold with fewer vent holes, resulting in raw materials savings. A typical steering wheel mold has from 8 to 20 vent holes depending on the size and complexity of a CFC-blown integral skin part. The vent holes serve to prevent excessive pressure buildup and poor skin formation and aid in the flow of material through complex shapes by allowing volatized blowing agent and urethane to escape through the hole. Without vent holes or with an inadequate number of vent holes, the trapped gases will form bubbles near the surface of the skin. To compensate for the raw material lost through the vent holes, anywhere from 25 to 75 weight percent excess of raw material is shot into the mold resulting in higher costs per part than would otherwise be necessary.

In the water-blown polyurethane system of the present invention, the lower molecular weight of water requires less water on a weight percentage to produce the same number of moles as CFC. It has been found, however, that using molds having the same number and size of vent holes suitable for use in CFC-blown systems produced a part with a substandard skin delaminating from the core, referred to as the formation of "onion skin." Without being bound to a theory, it is believed that this effect is due, at least in part, to an excess of carbon dioxide and raw material escaping through the vent hole with a large enough pressure drop within the mold to interfere with a satisfactory densification of raw material at the mold surface. It would seem that the pressures generated within the mold by the blowing action of carbon dioxide are not sufficient to solubilize that gas at the surface of the mold. By reducing the number of vent holes, the pressure within the mold is increased, possibly increasing the solubility of the gas in the raw material at the surface of the mold rather than escaping out of the raw material through the vent holes.

To make a good quality skin free of bubbles, pores, and which adheres well to the core, the number or number and size of the vent holes in the mold are reduced with the added advantage of reduced raw material waste. Thus, the amount of water-blown overall raw material needed to produce a part having a density equivalent to a part blown with a physically active blowing agent is reduced by approximately 10 weight percent to about 20 weight percent, the exact percentage reduction varying with the particular density of the part and complexity of the mold. For example, in a steering wheel mold which has 12–16 vent holes and requires 850 grams of raw material to make a 25–30 pcf part, only 4 or 5 vent holes of reduced size are required to make a water-blown part of comparable density using 750 grams of raw material.

The following examples are offered to illustrate various aspects of the invention. Those skilled in the art will appreciate that they are not limiting to the scope and spirit of the invention and various and obvious modifications will occur to those skilled in the art.

Polyol A is an all propylene oxide adduct of propylene glycol having a nominal hydroxyl number of 29.

Polyol B is a propylene oxide-ethylene oxide adduct of trimethylolpropane having a nominal hydroxyl number of about 26.6 and an average functionality of about 2.2.

Polyol C is a 66.7 part by weight Polyol B and a 33.3 part by weight Polyol A blend having about a 4.8 weight percent ethylene oxide cap and a nominal hydroxyl number of about 27.4.

Polyol D is a propylene oxide-ethylene oxide adduct of trimethylolpropane having a 13 weight percent ethylene oxide cap, a nominal hydroxyl number of about 35, and an average functionality of about 2.6.

Polyol E is Polyol D as a carrier for a graft polyol containing 31 weight percent of 1:1 acrylonitrile:styrene, the graft polyol having a nominal OH of 24.

Polyol F is a propylene oxide-ethylene oxide adduct of trimethylolpropane having about a 15 weight percent ethylene oxide cap, a nominal hydroxyl number of 25, and an average functionality of about 2.3.

Polyol G is a propylene oxide-ethylene oxide adduct of glycerine having an 18.5 weight percent ethylene oxide cap, a nominal hydroxyl number of 35, and an average functionality of about 2.6.

Polyol H is a 77/23 weight percent blend of Polyol E and Polyol D, respectively, having a nominal hydroxyl number of 26.7.

Polyol I is a propylene oxide-ethylene oxide adduct of glycerine having a 16.5 weight percent ethylene oxide cap, a nominal hydroxyl number of 35, and an average functionality of about 2.6.

Polyol J is a propylene oxide-ethylene oxide adduct of glycerine having a 21 weight percent ethylene oxide cap, a nominal hydroxyl number of 27.5, and an average functionality of about 2.5.

Polyol K is a propylene oxide-ethylene oxide adduct of dipropylene glycol having an 18 weight percent ethylene oxide cap, a nominal hydroxyl number of 56, and an average functionality of about 2.9.

Polyol L is a propylene oxide adduct of a glycerine/propylene glycol blend having a nominal hydroxyl number of 57.6 and an average functionality of about 2.7.

Isocyanate A is a 98 weight percent 4,4'-diphenylmethane diisocyanate having 2 weight percent of other MDI isomers, an NCO content of 33.6 weight percent, and a functionality of about 2.

Isocyanate B is a uretonimine-carbodiimide-modified 4,4'-MDI containing about 75 weight percent 4,4'-MDI and 25 weight percent of a uretonimine-carbodiimide-modified 4,4'-MDI, having an NCO content of about 29.5 weight percent.

Isocyanate C is a urethane-modified diphenylmethane diisocyanate containing 50 weight percent of quasi-prepolymer, the remainder being essentially 4,4'-MDI.

Isocyanate D is a polyphenylene polymethylene polyisocyanate having a functionality of approximately 2.7.

Isocyanate E is a diphenylmethane diisocyanate composition containing about 50 weight percent 2,4'-MDI, the remainder being essentially 4,4'-MDI.

Ethylene Glycol,

Diethylene Glycol, and Glycerine are chain extenders.

DABCO XFE 1027 is an amine used as a delayed action gel available from Air Products.

DABCO BL-11 is a 70 percent Bis(dimethylaminoethyl)ether; 30 percent dipropylene glycol (DPG) blowing catalyst available from Air Products.

DABCO BL-17 is a delayed action acid blocked version of DABCO BL-11, used as a blow catalyst, and available from Air Products.

DABCO HE is an amine catalyst providing delayed cream or faster demold, available from Air Products.

DABCO DC-1 is a delayed action amine-based gel catalyst available from Air Products.

DABCO 8154 is a delayed action acid blocked version of a 33 weight percent TEDA solution in dipropylene glycol available from Air Products.

UL-1 is an organotin catalyst available from WITCO Corp.

OXO-ALCOHOL is Lial 125, a linear $C_{12}$–$C_{15}$ alcohol composition available from Enichem Agusta.

X2-5384 is a silicone super wetting surfactant available from Air Products.

Uvinul A03 is an anti-oxidant available from BASF Corp.

Givsorb UV-1 is an ultraviolet stabilizer available from Givaudan Corp.

Gamma Butyrolactone is a plasticizer available from BASF Intermediates.

I-460 is a 75/25 weight percent BDO and TEDA, respectively, amine gel catalyst available from BASF Corp.

Tegostab B-2219 is a silicone cell stabilizing surfactant available from Goldschmidt.

TEST METHODS

Density ASTM D-1622
Tensile Elongation ASTM D412 Die A
Split Tear ASTM D-1938
Graves Tear ASTM D-412 Die C
Shore Hardness ASTM D-2240
Compression Set ASTM D-3574

Quasi-prepolymer 1

To a clean, dry, nitrogen-purged reactor is charged with about 54.5 weight percent molten Isocyanate A, about 21.6 weight percent Isocyanate B, and 0.003 weight percent benzoyl chloride. The ingredients are agitated under a nitrogen blanket throughout the reaction. The reactants are heated to about 60° C., after which about 23.9 weight percent of Polyol A is added at a constant rate over a one-hour period of time. The reaction is continued for the next three hours at 60°–65° C. and then cooled. The quasi-prepolymer had an NCO content of 24 weight percent and a viscosity of 120 cP at 25° C.

Quasi-prepolymer 2

The same procedure used to prepare Quasi-prepolymer 1 was employed in the preparation of Quasi-prepolymer 2, except that the new amounts were 65.3 weight percent of Isocyanate A, 5.9 weight percent of Isocyanate B, and about 28.8 weight percent of Polyol C instead of Polyol A. The quasi-prepolymer had an NCO content of 23 weight percent and a viscosity of 154 cP at 25° C.

Quasi-prepolymer 3

The same procedure followed to prepare Quasi-prepolymer 1 was employed except that the new amounts were 65.4 weight percent of Isocyanate A, 5.9 weight percent of Isocyanate B, and 28.6 weight percent of Polyol A, and the reactants were heated for two hours at about 80° C. after the Polyol was added.

The quasi-prepolymer had an NCO content of about 23 weight percent and a viscosity of about 143 cP at 25° C.

Quasi-prepolymer 4

To a clean, dry, nitrogen-purged reactor was added 61.104 weight percent molten Isocyanate A, 24.254 weight percent Isocyanate B, and 0.003 weight percent benzoyl chloride and agitated under a nitrogen blanket at 50°–60° C. To the mixture was added a polyol blend comprising 9.760 weight percent Polyol A and 4.879 weight percent dipropylene glycol at a constant rate over a one-hour period of time. The reactants were heated at 60° C. over the next two hours. The quasi-prepolymer had an NCO content of about 24.2 weight percent and a viscosity of about 246 cP at 25° C. The dipropylene glycol raised the viscosity by about 100 cP over Quasi-prepolymers 1, 2, and 3.

Quasi-prepolymer 5

The same procedure as used in Quasi-prepolymer 4 was employed except that the new amounts were 61.296 weight percent Isocyanate A, 24.331 weight percent Isocyanate B, 9.34 weight percent Polyol A, and 5.03 weight percent dipropylene glycol. The quasi-prepolymer had an NCO content of 24.2 weight percent and a viscosity of about 250.

Quasi-prepolymer 6

The same procedure as in Quasi-prepolymer 4 was followed, except using 90.0 weight percent Isocyanate B, 6.5 weight percent Polyol A, 3.5 weight percent dipropylene glycol, and seven (7) drops of benzoyl chloride. The quasi-prepolymer had an NCO content of 24.3 weight percent, a viscosity of 378 cP at 25° C., and was stored stable at 10° C. for a period in excess of three (3) weeks without crystalline formation.

Comparative Isocyanate 7

This isocyanate is a 50/50 blend of Isocyanate C and Isocyanate B, respectively, having an NCO content of about 26 weight percent.

Comparative Quasi-prepolymer 8

This isocyanate is a blend of about 78 weight percent Isocyanate C, about 16 weight percent Isocyanate D, and about 6 weight percent Isocyanate E.

Comparative Isocyanate 9

To a clean, dry, nitrogen-padded reaction vessel was charged 74.2 weight percent Isocyanate C, 15.4 weight percent Isocyanate D, and 5.4 weight percent Isocyanate E. The ingredients were blended at 25° C.±3° C. until homogeneous, after which 5.0 weight percent Freon-113 was charged and blended at 25° C. until homogeneous. The blend had an NCO content of about 23.7 weight percent.

I-Skin Foam Samples 1–5

Foam Sample 1 was made by reacting Quasi-prepolymer 1 with the resin component in the proportions indicated on Table 1 below. The resin component ingredients were combined according to the type and amounts stated in Table 1 below and mixed at 2,340 rpm using a 3" mixer blade for ten seconds at each successive addition of ingredients until all ingredients were added. Once the resin was mixed, it was shot into a Cannon L-mixhead and impingement mixed at 180 bar with Quasi-prepolymer 1 and shot into an 8"×8"×2" open preheated mold at about 220 gps throughput. The mold was closed and clamped while the system foamed. The part was demolded and submitted for testing, the results of which are reported in Table 2. The same procedure was followed to prepare Foam Samples 2–5, except that Sample 2 using Quasi-prepolymer 3 was run on a PU-15 machine.

TABLE 1

|  | FOAM SAMPLE | | | | |
|---|---|---|---|---|---|
|  | 1 | 2 | 3* | 4* | 5* |
| QUASI-PREPOLYMER 1 | 63.1 | | | | |
| QUASI-PREPOLYMER 3 | | 63.1 | | | |
| ISOCYANATE 7 | | | 58.8 | | |
| ISOCYANATE 8 | | | | 61.6 | |
| ISOCYANATE 9 | | | | | 46.3 |
| POLYOL D | | | | | 48.03 |
| POLYOL E | | | | | 22.42 |
| POLYOL F | | | | | 11.70 |
| POLYOL G | 60.98 | | | 60.98 | 60.98 |
| POLYOL H | 28.95 | | | 28.95 | 28.95 |
| POLYOL I | | 79.71 | | | |
| POLYOL E | | 10.0 | | | |
| ETHYLENE GLYCOL | 4.74 | 5.9 | | 4.74 | 4.74 |
| DIETHYLENE GLYCOL | 2.11 | | | 2.11 | 2.11 |
| GLYCERINE | | | | | .48 |

TABLE 1-continued

| | FOAM SAMPLE | | | | |
|---|---|---|---|---|---|
| | 1 | 2 | 3* | 4* | 5* |
| XFE 1027 | 0.63 | | 0.63 | 0.63 | |
| I-460 | | | | | 1.00 |
| DABCO BL-17 | | 0.1 | | | |
| DABCO BL-11 | 0.32 | | 0.32 | 0.32 | |
| DABCO HE | | 1.30 | | | |
| DABCO DC-1 | | | | | 0.14 |
| DABCO 8154 | | | | | 0.10 |
| UL-1 | 0.05 | | 0.05 | 0.05 | |
| OXO-ALCOHOL | 0.63 | 0.6 | 0.63 | 0.63 | |
| X 2-5384 | 0.21 | 0.5 | 0.21 | 0.21 | |
| TEGOSTAB B-2219 | | | | | 0.09 |
| UNIVUL A03 | 0.35 | | 0.35 | 0.35 | |
| GIVSORB UV-1 | 0.18 | | 0.18 | 0.18 | |
| WATER | 0.85 | 0.75 | 0.85 | 0.85 | |
| FREON F-11A (INHIBITED) | | | | | 10.49 |
| GAMMA BUTYROLACTONE | | 2.0 | | | |
| FOMREZ UL-24 | | 0.04 | | | |
| RESIN TOTAL | 100 | 100 | 100 | 100 | 100 |
| MIX RATIO (RESIN/ISO PBW) | 100/63.1 | 100/63.1 | 100/58.8 | 100/61.6 | 100/46.3 |
| PROCESSING DATA | | | | | |
| GASSING, BUBBLES, POROSITY | LITTLE TO NONE | SOME | YES | YES | |
| DEMOLD TIME (SECONDS) | 100 | 150 | 210 | 180 | |
| MOLD TEMPERATURE (F.) | 125 | 115 | 105 | 115 | |
| TANKS (RESIN AND ISO) | 75°–95° F. | 75°–95° F. | 75°–95° F. | 75°–95° F. | 70°–80° F. |

*COMPARATIVE

TABLE 2

| | SAMPLE | | | | |
|---|---|---|---|---|---|
| | 1 | 2 | 3* | 4* | 5* |
| DENSITY (OVERALL MOLDED) | 30 | 30.4 | 26 | 27 | 29 |
| SHORE A HARDNESS | 55 | 52 | 60 | 70 | 72 |
| AFTER 5 SECONDS | 56 | 49 | 51 | 69 | 69 |
| SKIN THICKNESS, IN. | 0.06 | 0.06 | | | 0.116 |
| TENSILE P.S.I., SKIN | *608.5 | 656 | 365 | 422 | 857 |
| SKIN AND CORE | 524.5 | 509 | | 333 | 510 |
| CORE | 226.3 | 324 | 202 | 221 | 219 |
| SPLIT TEAR, P.I., SKIN | 29.3 | 24 | 28 | 20.1 | 27 |
| SKIN AND CORE | 22.3 | 24 | | 16.9 | 19 |
| CORE | 18 | 16.5 | 12 | 10 | 8 |
| GRAVES TEAR, P.I., SKIN | 98 | 101 | 56 | 69 | 99 |
| SKIN AND CORE | 84.6 | 86.8 | | 52 | 53 |
| CORE | 47.2 | 61.3 | 30 | 36 | 23 |
| ELONGATION, %, SKIN | 208 | 226.7 | 170 | 165 | 127 |
| SKIN AND CORE | 203 | 203 | | | 123 |
| CORE | 187 | 190 | 128 | 156 | 117 |
| COMPRESSION SET, % | 15.4 | 25.5 | 80 | 90 | 19 |
| Taber ABRASION (MG. LOSS) | 67 | 144 | | | 69.3 |

*COMPARATIVE

The results indicate that the quasi-prepolymers and resin components used in the present invention, Samples 1 and 2, yield a foam having good overall mechanical properties, including compression set, compared to the CFC-blown Sample 5. The comparative foams made with the same resin component but differing isocyanates, Samples 3 and 4, exhibited poor compression sets and somewhat lower mechanical properties in other areas. The inventive Samples 1 and 2 with thinner skins also exhibited comparable mechanical properties to the Sample 5 CFC-blown system previously used to manufacture integral skin parts. In particular, the compression set values are close to or exceed the CFC-blown system, and the tensile strength, split tear strength, Graves tear strength, and elongation matches or exceeds the CFC-blown foam. Thus, the water-blown polyurethane system employed in the present invention is a replacement for CFC-blown foams in every respect.

The processing characteristics of Foam Samples 1 and 2 were also superior to those of Samples 3 and 4 with respect to faster demold times, higher limits on mold temperature, a wide range in tank temperatures, and few, if no, bubbles or pores on the surface of the skin.

FOAM SAMPLE 6

In this test, a 34 pcf microcellular polyurethane 1" plaque was made by impingement mixing 212.3 grams of Quasi-Prepolymer 2 with 353.7 grams of a resin composition according to the procedure used to make Foam Samples 1-5. The resin composition comprised 65.48 weight percent Polyol J, 10 weight percent Polyol E, 16 weight percent Polyol K, 5 weight percent ethylene glycol, 1.1 weight percent DABCO XFE-1027 catalyst, 0.5 weight percent DABCO BL-17, 0.6 weight percent X2-5384 surfactant, 0.7 weight percent oxo-alcohol, 0.02 UL-1 catalyst, and 0.6 weight percent water. The 1" plaque was tested for physical properties and the following results were obtained:

Shore A Hardness 50
Tensile 560 psi
Elongation 400 percent
Split Tear 42 pi
Tabor Abrasion 157 mg/loss.

The physical data indicates that this water-blown integral skin polyurethane molded article is also a useful alternative to CFC-blown integral skin applications such as shoe soles.

We claim:

1. A polyurethane integral skin foam obtained by reacting a quasi-prepolymer component with a resin component, said quasi-prepolymer comprising:
  A) the reaction product of from 0.5 weight percent to 30.0 weight percent or less uretonimine-carbodiimide-modified 4,4'-diphenylmethane diisocyanate and from 50 weight percent to 80 weight percent 4,4'-diphenylmethane diisocyanate with from 15 weight percent to 40 weight percent of a polyether polyol composition containing a predominant amount of secondary hydroxyl groups and having an average molecular weight from 2,000 to 10,000 and an average functionality from 1.5 to 3.2; said resin component comprising:

B) a composition having isocyanate reactive hydrogens, an average molecular weight from 2,000 to 10,000 and an average functionality from 1.5 to 3.2;
C) a chain extender;
D) a polyurethane and/or polyurea promoting catalyst;
E) a surfactant;
F) a blowing agent comprising water; and,
G) optionally a branched and/or unbranched alcohol composition having from 6 to 20 carbons.

2. The foam of claim 1, wherein the foam is water blown, and the amount of uretonimine-carbodiimide modified 4,4'-diphenylmethane diisocyanate is less than 12.5 weight percent.

3. The foam of claim 2, wherein the ratio of uretonimine to carbodiimide ranges from 85-99:15-1.

4. The foam of claim 2, wherein the quasi-prepolymer is made in the presence of a catalyst deactivator comprising an acid chloride.

5. The foam of claim 2, wherein the amount of uretonimine-carbodiimide-modified 4,4'-diphenylmethane diisocyanate is from 4.0 weight percent to 6.5 weight percent.

6. The foam of claim 5, wherein the amount of 4,4'-diphenylmethane is from 65 weight percent to 75 weight percent.

7. The foam of claim 5, wherein the polyether polyol composition consists of a polyoxypropylene polyether polyol composition prepared by reacting propylene oxide with an initiator having at least two hydrogens reactive with propylene oxide.

8. The foam of claim 7, wherein the initiator is propylene glycol.

9. The foam of claim 7, wherein the amount of polyether polyol in the quasi-prepolymer is from 20 weight percent to 30 weight percent.

10. The foam of claim 9, wherein the polyether polyol has an average molecular weight from 3,000 to 3,600.

11. The foam of claim 2, wherein the quasi-prepolymer has an NCO content of 22 weight percent to 26 weight percent.

12. The foam of claim 2, wherein a diol, triol, or tetrol having a molecular weight of less than 175 is blended with the polyether polyol composition in an amount of from 1.0 weight percent to 10 weight percent.

13. The foam of claim 2, wherein water is present in an amount of from 0.4 weight percent to 1.0 weight percent based on the weight of the resin component.

14. The foam of claim 2, wherein the resin contains the alcohol composition, is comprised of a mixture of alcohols having from 12 to 15 carbons, and is present in amounts from 0.3 weight percent to 1.0 weight percent based on the weight of the resin component.

15. The foam of claim 2, wherein the chain extender is selected from the group consisting of ethylene glycol, diethylene glycol, 1,4-butanediol, propylene glycol, and mixtures thereof.

* * * * *